US00PP28432P3

(12) United States Plant Patent
Frank

(10) Patent No.: US PP28,432 P3
(45) Date of Patent: Sep. 19, 2017

(54) ***ORNITHOGALUM* PLANT NAMED 'MFYELLSTAR'**

(50) Latin Name: *Ornithogalum dubium*
Varietal Denomination: MFYELLSTAR

(71) Applicant: Michael Frank, Moshav Givat Chen (IL)

(72) Inventor: Michael Frank, Moshav Givat Chen (IL)

( * ) Notice: Subject to any disclaimer, the term of this patent is extended or adjusted under 35 U.S.C. 154(b) by 21 days.

(21) Appl. No.: 14/756,134

(22) Filed: Aug. 4, 2015

(65) Prior Publication Data

US 2017/0042077 P1 Feb. 9, 2017

(51) Int. Cl.
*A01H 5/02* (2006.01)

(52) U.S. Cl.
USPC ..... Plt./462

(58) Field of Classification Search
USPC ..... Plt./462
See application file for complete search history.

*Primary Examiner* — Keith Robinson
(74) *Attorney, Agent, or Firm* — Cassandra Bright

(57) ABSTRACT

A new and distinct *Ornithogalum* cultivar named 'MFYELLSTAR' is disclosed, characterized by sterility, long inflorescence of 30 cm, height of 60 cm, a high yield of 2-3 inflorescence per bulb and yellow flower petals. The new variety is an *Ornithogalum*, normally produced as an ornamental plant or cut flower.

1 Drawing Sheet

Latin name of the genus and species: *Ornithogalum dubium.*

Variety denomination: 'MFYELLSTAR'.

BACKGROUND OF THE INVENTION

The new *Ornithogalum* cultivar is a product of a planned breeding program conducted by the inventor, Michael Frank, in Moshav Givat Chen, Israel. The objective of the breeding program was to produce new *Ornithogalum* varieties for ornamental commercial applications. The cross resulting in this new variety was made during March of 2012.

The seed parent is the, unpatented, commercial variety referred to as *Ornithogalum* 'MFGOLDSTAR'. The pollen parent is the unpatented, commercial variety referred to as *Ornithogalum* 'MFSSTAR'. The new variety was discovered in March of 2013 by the inventor in a group of seedlings resulting from the 2012 crossing, in a research greenhouse in Moshav Givat Chen, Israel.

Asexual reproduction of the new cultivar was performed by tissue culture. This was first performed at a research laboratory in Moshav Givat Chen, Israel in March of 2013 and has shown that the unique features of this cultivar are stable and reproduced true to type in multiple successive generations.

SUMMARY OF THE INVENTION

The cultivar 'MFYELLSTAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MFYELLSTAR' These characteristics in combination distinguish 'MFYELLSTAR' as a new and distinct *Ornithogalum* cultivar:

1. Yellow petals
2. Long inflorescence (30 cm)
3. Average height 60 cm
4. Sterile
5. 150 days to flowering

PARENT COMPARISON

Plants of the new cultivar 'MFYELLSTAR' are similar to plants of the seed parent, *Ornithogalum* 'MFGOLDSTAR' in most horticultural characteristics, however, plants of the new cultivar 'MFYELLSTAR' differ in the following;

1. Yellow flowers, while the seed parent has a dark yellow flower.
2. Has a 30 cm long Inflorescence, while the seed parent has 10 cm long inflorescence.
3. Height is 60 cm, while the seed parent is 50 cm.
4. Sterile, while the seed parent is fertile.

Plants of the new cultivar 'MFYELLSTAR' are similar to plants of the pollen parent, *Ornithogalum* 'MFSSTAR' in most horticultural characteristics, however, plants of the new cultivar 'MFYELLSTAR' differ in the following;

1. Sterile, whereas the pollen parent is fertile.
2. 30 cm long inflorescence, whereas the pollen parent has 20 cm long inflorescence.
3. Flowers color is yellow, while the pollen parent has orange flowers.

COMMERCIAL COMPARISON

Plants of the new cultivar 'MFYELLSTAR' are comparable to the unpatented commercial variety *Ornithogalum* 'MFWHITSTAR'. The two *Ornithogalum* varieties are similar in most horticultural characteristics; however, the new variety 'MFYELLSTAR' differs in the following:

1. The new variety has yellow flowers, the comparator has white flowers.
2. The new variety height is 60 cm, the comparator is 55 cm in height.
3. The new variety has smooth scape, the comparator has a textured scape.
4. The new variety is sterile, the comparator is fertile.

BRIEF DESCRIPTION OF THE PHOTOGRAPH

The accompanying photograph in FIG. 1 illustrates in full color a close up of the flowering stem. The stem was harvested from a plant of approximately 6 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'MFYELLSTAR' plants grown outdoors and in greenhouse during the Spring and Summer in Moshav Givat Chen, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Ornithogalum dubium* 'MFYELLSTAR'.

PROPAGATION

Time to initiate roots: About 3 days at approximately 20° C.
Root description: Adventive.
Propagation method: Tissue culture.
Bulb description:
- *Color*.—Mixture of Brown 200C, 200D, Greyed-Orange 177A and 174A.
- *Diameter*.—6-16 mm for first year bulbs (5 month growth).
- *Height*.—6-20 mm for first year bulbs (5 month growth).

PLANT

Age of plant described: Approximately 5 months.
Pot size of plant described: Planted in soil.
Typical time to produce a flowering plant commercially: 150-180 days.
Height: Approximately 40 cm to top of highest leaf. Approximately 60 cm to top of highest inflorescence.
Plant spread: Approximately 25 cm.
Growth rate: High.
Branching characteristics: Non-branching.

FOLIAGE

Leaf:
- *Arrangement*.—Rosette.
- *Average length*.—Approximately 25 cm.
- *Average width*.—Approximately 5 cm.
- *Shape of blade*.—Sharp tip, flattened.
- *Apex*.—Sharp tip.
- *Base*.—Flattened.
- *Margin*.—Smooth.
- *Texture of top surface*.—Smooth.
- *Texture of bottom surface*.—Smooth.
- *Quantity of leaves per plant*.—Approximately 7.
- *Attitude*.—Arched.
- *Color*.—Between Green 141C and 137C.
- *Venation*.—Type: Linear.

FLOWER

Natural flowering season: Spring
Time to flowering: About 150 days.
Flowering stems produced per bulb: 2-3.
Inflorecence type and habit: Long raceme.
Rate of flower opening: 3-5 days from pigments formation.
Flower longevity on plant, or in vase if cut flower: 6 weeks and 3 weeks respectively.
Quantity of flowers per inflorescence: 40.
Average inflorescence per plant: 1.
Inflorescence size:
- *Height*.—Approximately 30 cm.
- *Width*.—Approximately 4 cm.

Flowers per inflorescence: Average 25.
Individual flowers:
- *Length*.—Approximately 3 cm.
- *Width*.—Approximately 3 cm.
- *Type*.—Single.
- *Shape*.—Cup.
- *Petals*.—Quantity: 6. Shape: Elliptic, concave. Length: Approximately 1.5 cm. Width: Approximately 1 cm. Margin: Smooth. Apex: Tip-like. Base: Smooth. Texture: Smooth inner and outer surfaces. Appearance: Matte inner and outer surfaces.

Color:
- *Petals*.—When opening: Outer surface: Near RHS Yellow 3A. Inner surface: Near RHS Yellow 3A. Fully opened: Outer surface: Near RHS Yellow 3A. Inner surface: Near RHS Yellow 3A. Color Changes when Aging: Yes. Streaks or blotches of White 155C.
- *Striations or marking*.—Absent.
- *Sepals*.—Quantity: 40. Shape: Concave blade-like. Length: Approximately 2-5 cm. Width: Approximately 1 cm. Margin: Smooth. Apex: Sharp tip. Base: Smooth. Texture: Smooth inner and outer surfaces. Appearance: Matte inner and outer surfaces.

Color:
- *Sepals*.—When opening: Green. Outer surface: Near RHS Yellow-Green 144C. Inner surface: Near RHS. Yellow-Green 144C. Fully opened: Outer surface: Near RHS Yellow-Green 144C. Inner surface: Near RHS Yellow-Green 144C.

Bud:
- *Shape*.—Conic.
- *Length*.—Approximately 1 cm.
- *Diameter*.—Approximately 0.5 cm.
- *Color*.—Near RHS Yellow-Green N144C, flushed Yellow 3C.

Pedicels:
- *Length*.—Approximately 3 cm.
- *Width*.—Approximately 0.01 cm.
- *Aspect*.—Angular.
- *Strength*.—Firm.

*Texture*.—Smooth.
*Color*.—Near RHS Yellow-Green 144B.

Scape:
*Length*.—Approximately 60 cm.
*Width*.—Approximately 1 cm.
*Texture*.—Smooth.
*Angle*.—Erect.
*Strength*.—High.
*Color*.—Near RHS Yellow-Green N144C.

Bract:
*Length*.—5 mm.
*Form*.—Ovate.
*Color*.—Near RHS Green 137B.

Fragrance: None.

REPRODUCTIVE ORGANS

Stamens:
*Number*.—6.
*Filament length*.—Approximately 0.4 cm.
*Filament color*.—Near RHS Yellow-Green N144C.
*Anther length*.—0.3 cm.
*Anther color*.—Near RHS Yellow 3A.
*Anther shape*.—Tag-like.
*Pollen*.—No pollen (sterile).

Pistil:
*Number*.—1.
*Length*.—Approximately 0.3 cm.
*Style color*.—Near RHS Black 202A.
*Stigma*.—Shape: Trilobed. Color: Near RHS Black 202A. Ovary color: Near RHS Yellow-Green N144C.

OTHER CHARACTERISTICS

Seeds and fruits: Completely infertile, no seeds or fruit produced.

Disease/pest resistance: Relatively resistance to *Erwinia corotovora*. Neither resistance nor susceptibility to other normal diseases and pests of *Ornithogalum* has been observed.

Temperature tolerance: Tolerates temperatures from approximately 1° C. to 30° C.

What is claimed is:

1. A new and distinct cultivar of *Ornithogalum* plant named 'MFYELLSTAR' as herein illustrated and described.

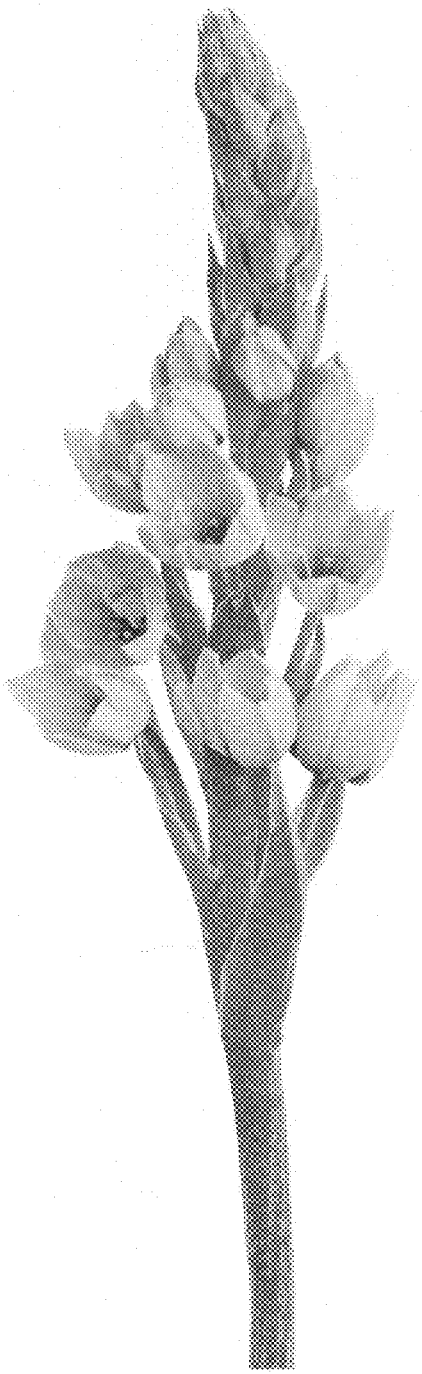

* * * * *